(12) United States Patent
Blum et al.

(10) Patent No.: US 8,052,009 B2
(45) Date of Patent: Nov. 8, 2011

(54) ADHESIVE BANDAGE AND DISPENSER

(76) Inventors: Walter Blum, Great Neck, NY (US);
Nico Roger, Great Neck, NY (US)

( * ) Notice: Subject to any disclaimer, the term of this patent is extended or adjusted under 35 U.S.C. 154(b) by 253 days.

(21) Appl. No.: 12/387,141

(22) Filed: Apr. 28, 2009

(65) Prior Publication Data

US 2010/0270324 A1    Oct. 28, 2010

(51) Int. Cl.
*B65H 5/28* (2006.01)
*B65D 83/08* (2006.01)

(52) U.S. Cl. .............. 221/73; 221/25; 221/41; 221/45; 221/26; 221/312 R

(58) Field of Classification Search .............. 221/25, 221/311, 312 R, 41, 45, 55, 33, 22, 26, 73
See application file for complete search history.

(56) References Cited

U.S. PATENT DOCUMENTS

| | | | |
|---|---|---|---|
| 2,367,417 A | | 1/1945 | Milem |
| 2,373,092 A | * | 4/1945 | Avery ............................... 221/1 |
| 2,646,877 A | | 7/1953 | Scholl |
| 2,822,046 A | | 2/1958 | Krueger |
| 3,530,494 A | | 9/1970 | Baratta |
| 3,835,992 A | | 9/1974 | Adams, IV |
| 4,676,861 A | * | 6/1987 | Bishop .......................... 156/527 |
| 4,735,342 A | | 4/1988 | Goldstein |
| 4,807,753 A | | 2/1989 | Goldstein |
| 4,824,517 A | * | 4/1989 | Leahy ............................ 156/584 |
| 4,993,586 A | * | 2/1991 | Taulbee et al. .................. 221/25 |
| 5,003,970 A | | 4/1991 | Parker et al. |
| 5,133,477 A | | 7/1992 | Etheredge, III et al. |
| 5,782,786 A | | 7/1998 | Tomaiuolo |
| 5,792,092 A | * | 8/1998 | Turngren ......................... 602/58 |
| 5,981,823 A | | 11/1999 | Turngren |
| 6,213,343 B1 | * | 4/2001 | Damikolas ....................... 221/25 |
| 6,756,519 B2 | | 6/2004 | Johnson et al. |
| 7,588,548 B2 | * | 9/2009 | Kopreski ........................... 602/2 |
| 7,683,235 B2 | * | 3/2010 | Wendorf .......................... 602/57 |
| 7,748,531 B2 | * | 7/2010 | O'Hara .......................... 206/409 |
| 2003/0150896 A1 | | 8/2003 | Michel |
| 2007/0068837 A1 | * | 3/2007 | D'Angelis .................... 206/440 |

* cited by examiner

*Primary Examiner* — Michael K Collins
(74) *Attorney, Agent, or Firm* — Collard & Roe, P.C.

(57) ABSTRACT

A bandage dispensing device dispenses bandages with an upper protective layer of its packaging removed so that a person can dispense a bandage using only one hand. A separator placed near an opening in a wall of the housing of the device separates the upper protective layer from a roll of interconnected bandages so that only a bandage and a lower protective layer emerge from the housing of the device. The separator has at least one arm that protrudes from the side wall of the housing in a perpendicular direction and separates an upper protective layer of the packaging. The upper protective layer that has been separated by the separator gathers inside of the housing. In the roll of packaged bandages, the upper protective layer is releasably attached to the lower protective layer.

14 Claims, 4 Drawing Sheets

ADHESIVE BANDAGE AND DISPENSER

BACKGROUND OF THE INVENTION

1. Field of the Invention

This invention relates to a dispenser for adhesive bandages that facilitates the removal of an individual adhesive bandage and its adhesive packaging from a roll of interconnected adhesive bandages.

2. The Prior Art

Adhesive bandages are widely used. They are generally comprised of a small square of gauze bandage attached to an adhesive strip. The adhesive portions have a removable backing to preserve the adhesive force of the bandage. The bandage is usually wrapped in a protective wrapping to help preserve its sterility prior to use, with the outer packing particularly preserving the sterility of the gauze that would otherwise be uncovered.

While these bandages are widely used, it is often inconvenient to attempt to remove an individual adhesive bandage from its packaging prior to use, especially when the injured person is the one trying to open the packaging, and more especially when the injury is to that person's hand or arm.

U.S. Pat. Nos. 4,807,753 and 4,735,342 to Goldstein disclose a housing for a roll of bandages with an opening in the housing through which an individual bandage can be passed. One bandage with packaging is removed from the roll of bandages as it free from the roll at a transverse line of weakness in the interconnected packaging. The bandage projects out of the end of the packaging so that removing the top and bottom parts of the packaging is easier, because any transverse seal of the packaging at that end is already broken.

This dispenser usually requires two hands to be used to separate one individually packaged bandage from the roll of bandages. The structure of the dispenser facilitates storing bandages, but separating one bandage will usually require pulling that bandage with one hand while steadying or supporting with the other hand the bandage meant to be left attached to the roll.

U.S. Pat. No. 4,993,586 to Taulbee, deceased et al. discloses an adhesive bandage dispensing device with a roll of connected individual adhesive bandages hanging on a spool of a housing. The lead bandage is pulled through a slicer housing that has two vertical blades spaced apart so that the blades cut the bandage packaging on the side edges of the packaging. This cutting allows the individual bandage to be easily removed from the packaging. The slicer housing is placed on one top end of the device. After being cut by the slicer housing, the packaging can be cut transversely to be removed from the rest of the roll by a cutter comprising jagged edges or teeth placed along a top edge of the device on the opposite end.

However, proper functioning of the device of Taulbee, deceased et al. depends on the cutting of vertical blades which can become dull over time and require replacement. As the blades become duller, an increasing amount of physical force is required for pulling on the bandage to let the vertical blades cut the sides of the bandage packaging. Using blades to make this cut can also lead to jamming of the device.

Thus, a need exists for a bandage dispensing device that allows a one-handed removal of a bandage from its packaging without depending on physical cutting with blades.

SUMMARY OF THE INVENTION

A bandage dispensing device is provided that allows one-handed removal of a bandage from its packaging without depending on physical cutting with blades. The device comprises a housing for accommodating a roll of separable packaged bandages. Each packaged bandage of the roll has a top protective layer and a bottom protective layer. The housing has an opening in a wall thereof so that the packaged bandages can be pulled out of the housing.

A separator is disposed within the housing, and comprises a separating arm that is adapted to separate a top protective layer of each packaged bandage from the bandage and from a bottom protective layer of the packaged bandage. The separating arm is inserted between the top protective layer and the bandage at the end of the roll of bandages within the housing. This allows the separator to separate the top protective layer from the bandages and the bottom protective layer in a continuous manner as the bandages and the bottom protective layer are pulled through the opening in the housing.

The separator can be a straight segment connected to the housing and the separating arm can extend from the straight segment and curve away from the straight segment so that an end of the separating arm is disposed perpendicular to the straight segment and towards an interior of the housing. The separator can have a second separating arm that is disposed on one end of the straight segment of the separator with the other separating arm being disposed on the opposite end of the straight segment. In this instance, the two separating arms extend in the same direction.

In one embodiment of the dispenser, any top protective layer that is separated from the roll of bandages by the separator, as the bandages and the bottom protective layer are pulled through the opening can remain inside the housing after the top protective layer is separated.

This can be done with an upper compartment in the housing that stores the top protective layer that has been separated from bandages and lower protective layer. The upper compartment holds this separated upper protective layer to prevent it from mixing with the roll of bandages in the housing.

The packaged bandages are connected to one another at their ends to form a continuous strip. Each individually packaged bandage comprises a bandage disposed between the top protective layer and a bottom protective layer, with the top protective layer being removably connected to the bottom protective layer via a releasable adhesive. The continuous strip of packaged bandages is arranged in a roll.

The bottom protective layer can have perforations that run in a transverse direction to the continuous strip. These perforations are found at the conjunction between individually wrapped bandages and facilitate in the separation of one packaged bandage from the adjacent bandage in the continuous strip.

A support for the roll of bandages can be connected to a side wall of the housing of the device. This support can be a rod.

The dispenser can have a cutting device disposed along a top or bottom side of the opening in the housing. This cutting device is adapted to separate a portion of the bottom protective layer from the roll of bandages by cutting, when the lower protective layer is pulled in a direction that presses the lower protective layer at the opening against the cutting device after the bandage and a portion of the lower protective layer have been pulled through the opening.

The advantage of the present invention is that it allows one-handed removal of the bandage from the housing, without requiring separate removal of the protective packaging of the bandage. The separator removes the top protective layer from the bandage, so that all that is required is to pull on the end of the bottom protective layer that protrudes from the housing in order to remove a bandage. Once the bottom layer has been pulled through, a sterile, unwrapped bandage is available for immediate use. The top and bottom protective layers keep the bandage sterile while in the housing, but can be easily removed by the separator so that the user does not have to struggle with unwrapping the bandage.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, similar reference characters denote similar elements throughout the several views.

DETAILED DESCRIPTION OF THE PREFERRED EMBODIMENT

Figure 1:
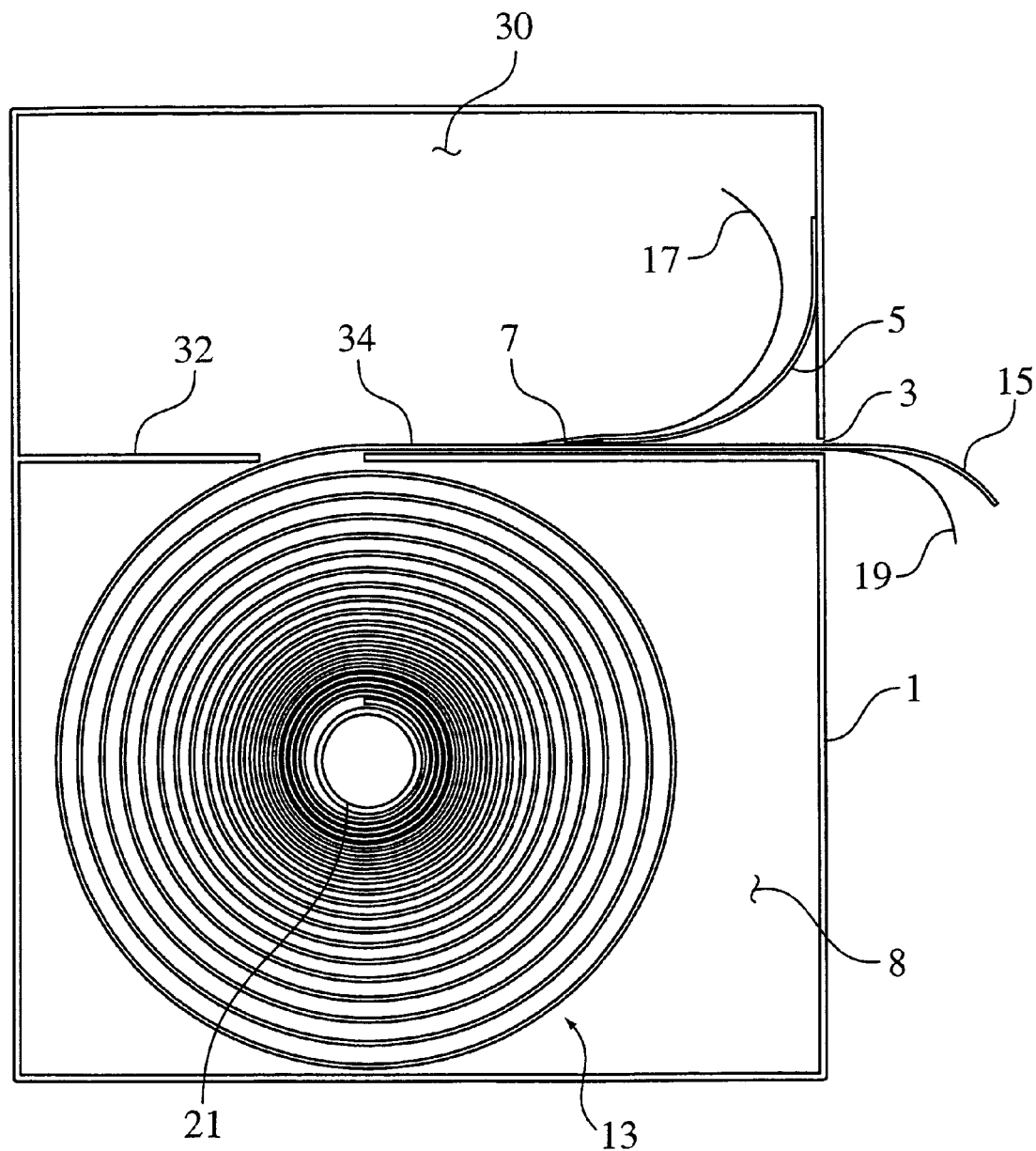
FIG. 1 shows a side interior view of the device loaded with a roll of adhesive bandages with the separator having separated some of the top protective layer from a bandage and from the bottom protective layer.

Referring now in detail to the drawings, the bandage dispenser shown in FIG. 1 is a housing 1 with an opening 3 in a side wall 4 of housing 1 and a separator 5 for separating top protective layer 17 of a roll of adhesive bandages 13. Roll of adhesive bandages 13 is a continuous strip of bandages 15 having a bottom protective layer 19 and top protective layer 17 attached thereto. Roll of adhesive bandages 13 is supported by a rod or a support 21 in the housing. Separating arm 7 of separator 5 is inserted between top protective layer 17 and bandages 15 of roll of adhesive bandages 13 to continually separate top protective layer 17 from bandages 15 and from bottom protective layer 19 as bandages 15 and bottom protective layer 19 are pulled through opening 3. Top protective layer 17 remains in housing 1 after it has been separated from bandages 15 and from bottom protective layer 19. Ideally, top protective layer 17 rolls around itself as subsequent bandages are removed from housing 1 and is retained in upper compartment 30. Bandage 15 and bottom protective layer 19 have been pulled out of housing 1 through opening 3. The view of FIG. 1 is directly at side wall 8 of housing 1.

Upper protective layer 17 that has been separated from bandages 15 and bottom protective layer 19 in housing 1 can be kept in upper compartment 30, which prevents the separated upper protective layer 17 from mixing with and disturbing operation of roll of bandages 13. Upper compartment 30 can be formed by platform 32 which can be connected to all of the side walls (which includes 4 and 8) of housing 1. Platform 32 can have a slot 34 near the end of separating arm 7 of separator 5 through which roll of bandages 13 can be pulled into upper compartment 30 from storage below upper compartment 30. Bandages 15 and lower protective layer 19 can slide on platform 32 towards opening 3 underneath separator 5 after upper protective layer 15 has been separated from bandages 15 and lower protective layer 19.

Figure 2:
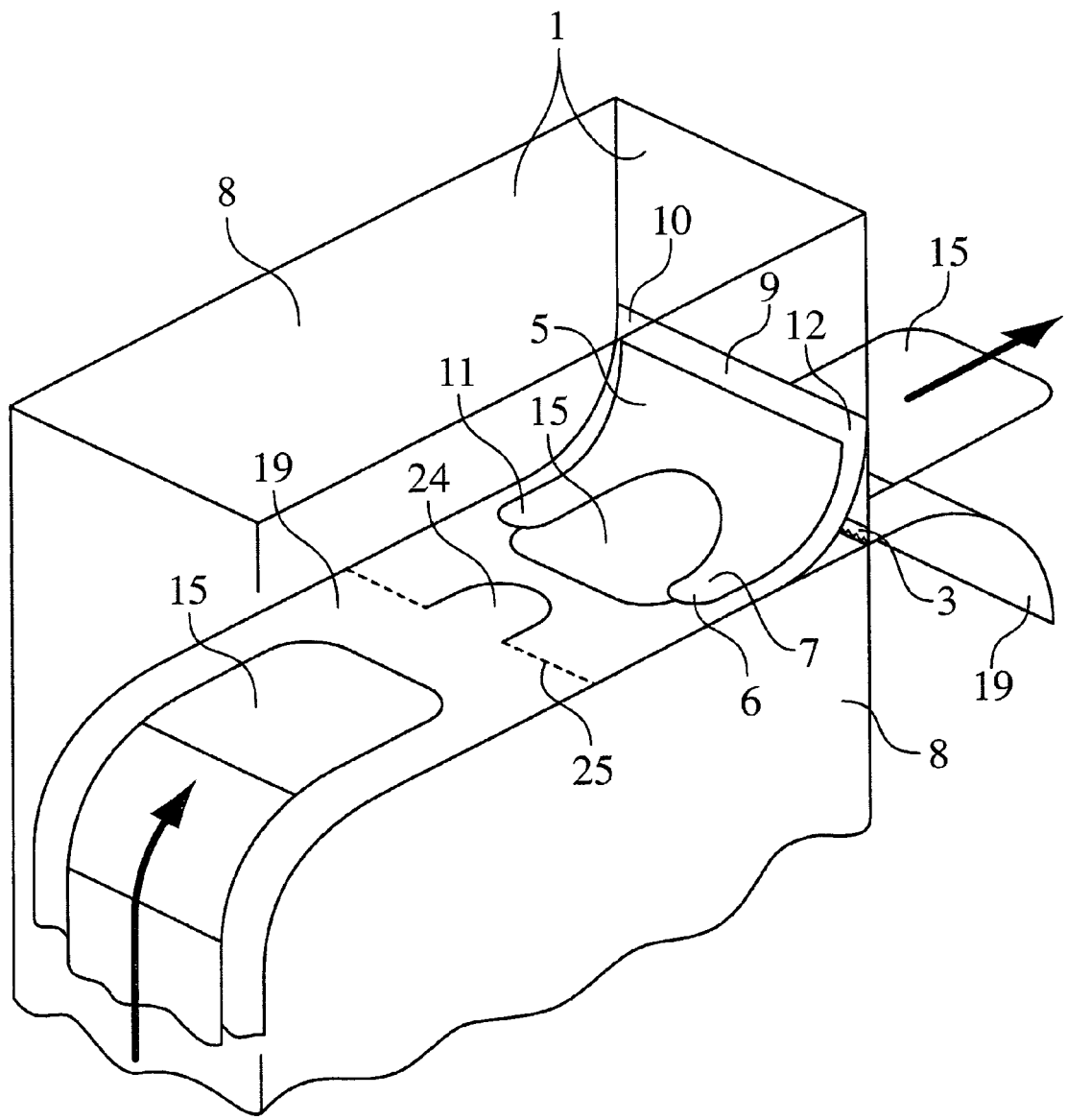
FIG. 2 shows a view of the inside of the housing from a top angle where the top protective layer is not seen so that a better view of the separator is provided.

FIG. 2 shows an interior view of the housing 1, in which separator 5 with a separating arm 7 and a second separating arm 11 are disposed. Straight segment 9 of separator 5 is connected to housing 1. Separating arm 7 and second separating arm 11 extend from straight segment 9 and curve away from the straight segment 9 so that an end 6 of separating arm 7 is disposed perpendicular to straight segment 9 and is disposed towards an interior of housing 1. Separating arms 7 and 11 of separator 5 are disposed on opposite ends 12 and 10 of straight segment 9, respectively. Separating arms 7 and 11 extend in the same direction. With the arrows, FIG. 2 shows the direction that bandages 15 and bottom protective layer 19 are pulled underneath separator 5 to allow separator 5 to separate top protective layer (not shown in FIG. 2) from bandages 15 and from bottom protective layer 19. Because the top protective layer is not shown in FIG. 2, bandages 15, bottom protective layer 19, and transverse perforations 25 are seen.

Figure 3:
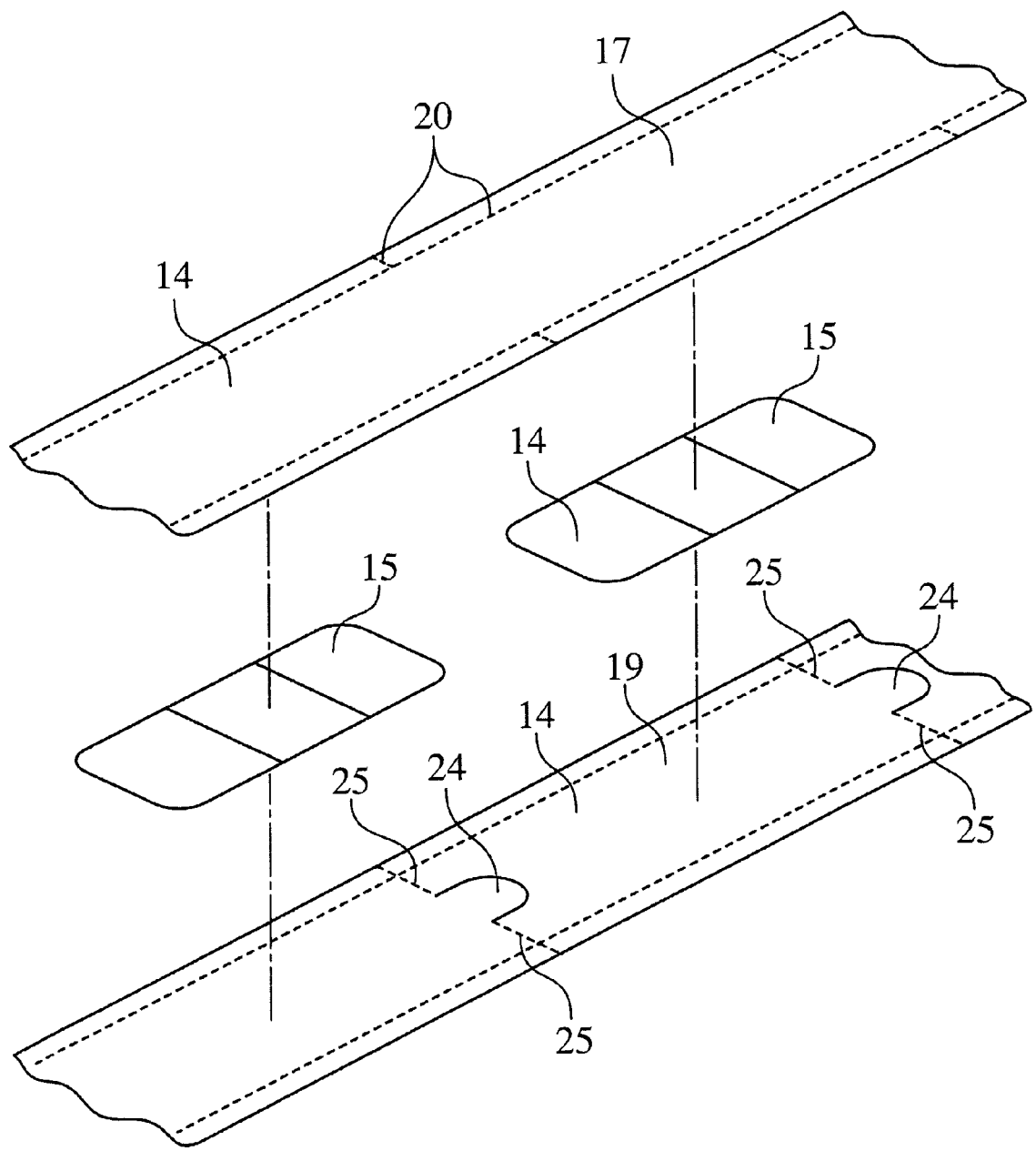
FIG. 3 shows separated components of the roll of adhesive bandages.

FIG. 3 shows a top protective layer 17 and a bottom protective layer 19 of a roll of adhesive bandages, and bandages 15 that are located between top protective layer 17 and bottom protective layer 19 in the roll. One packaged bandage 14 is made of one bandage 15 located between one portion of top protective layer 17 and one portion of bottom layer 19, between perforations 25. Perforations 25 in the bottom layer 19 run in a transverse direction to the direction that the bottom layer 19 is pulled out of the housing. Perforations 25 facilitate easier removal of a portion of bottom protective layer 19 from the rest of the bottom protective layer 19 in the roll of adhesive bandages. This removal will usually occur as the bottom protective layer is pulled against cutting device 23 in opening 3, shown in FIG. 5. A pull tab 24 protrudes at the end of the bottom protective layer 19 of one adhesive bandage 14.

Figure 4:
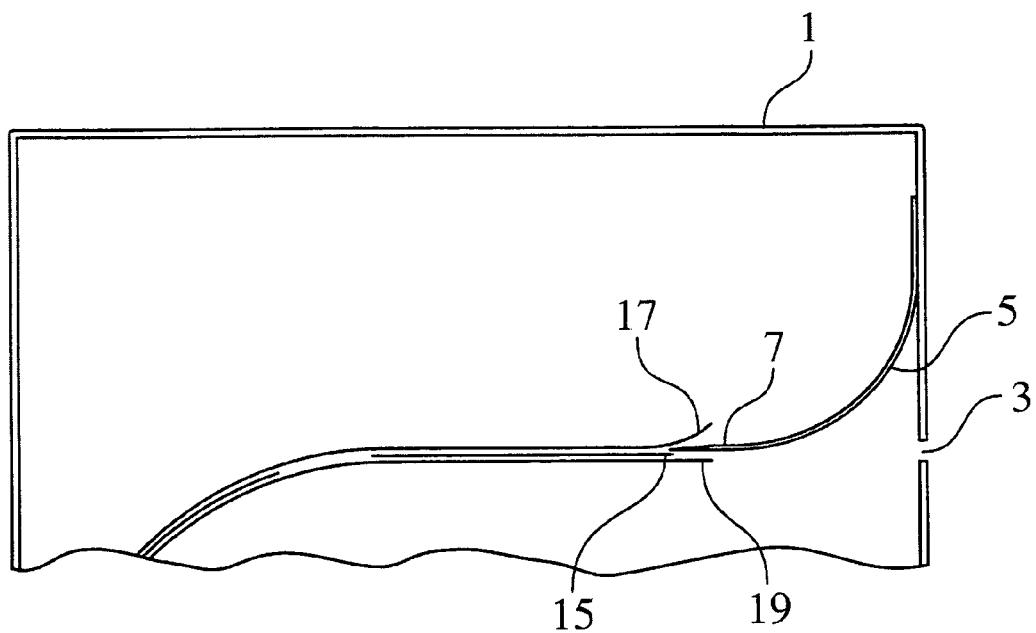
FIG. 4 shows a side view of the device with the side wall removed, to show a roll of adhesive bandages is first being loaded into the device, wherein the top protective layer at the end of the roll has been detached from the bandages and from the bottom protective layer.

FIG. 4 shows a top protective layer 17 at an end of the roll of adhesive bandages detached from the bottom protective layer 19 so that separating arm 7 is inserted between this portion of top protective layer 17 and bandage 15. The top protective layer 17 is separated by separating arm 7 from bandages 15 and from the bottom protective layer 19 as bandages 15 and bottom protective layer 19 are pulled towards opening 3. FIG. 4 shows a part of a beginning of the separation of top protective layer 17 from bandages 15 and from bottom protective layer 19.

Figure 5:
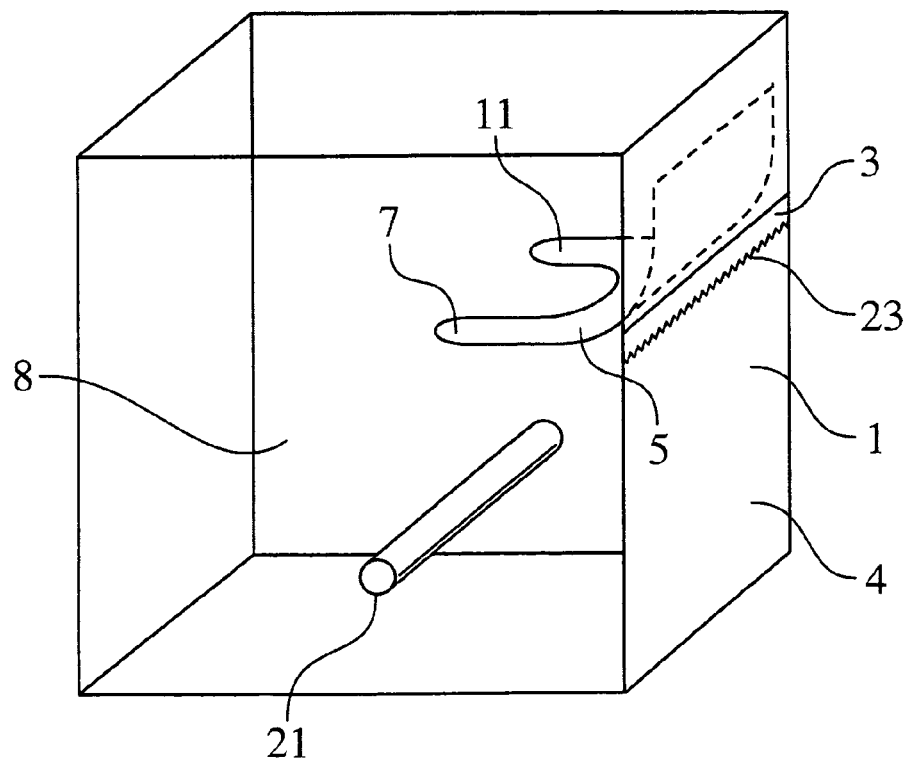
FIG. 5 shows a view of the device with a wall of the housing removed and with no bandages loaded into the device.

FIG. 5 shows a support a rod 21 connected to a side wall 8 of the housing 1 for supporting a roll of adhesive bandages in housing 1 of the device. Cutting device 23 is disposed along a bottom side of opening 3. Cutting device 23 is adapted to separate a portion of bottom protective layer 19 from the roll of adhesive bandages in the housing 1 at the opening 3 after a portion of the bottom protective layer 19 and a bandage 15 have been pulled through the opening 3. The bottom protective layer 19 is pulled against the cutting device 23 to separate this front portion of the bottom protective layer by cutting. Transverse perforations 25 (shown in FIGS. 2 and 3) in bottom protective layer 19 facilitate this separation of a portion of bottom protective layer 19 from the rest of bottom protective layer 19 in housing 1 of the device. After cutting device 23 cuts off bottom protective layer 19 that is outside of housing 1, a pull tab 24 (shown in FIG. 3), attached to the next portion of bottom protective layer 19 inside the housing, can protrude out of the opening so that the user can grab it and pull it to bring another bandage 15 and more bottom protective layer 19 outside of housing 1.

The bandage dispenser allows bandages to be dispensed without requiring cutting to separate a top protective layer of a roll of bandages from the bandages and from a bottom protective layer. The top protective layer of a roll of bandages is releasably attached to a bottom protective layer of a roll of bandages. The separator, which can be made of metal or plastic, acts to peel off the top protective layer from the bottom protective layer as it separates the top protective layer that is releasably attached to the bottom protective layer via a releasable adhesive. Releasable adhesive can be placed intermittently on top protective layer 17, as shown at 20 in FIG. 3.

While only one embodiment of the present invention has been shown and described, it is obvious that many changes and modifications may be made thereunto without departing from the spirit and scope of the invention.

What is claimed is:

1. A bandage dispenser for dispensing a roll of separable packaged bandages, wherein each packaged bandage of the roll has a top protective layer and a bottom protective layer, the dispenser comprising:
   a housing for accommodating the roll, the housing having an opening in a wall thereof so that the packaged bandages can be pulled out of the housing; and
   a separator disposed within the housing, said separator comprising a straight segment connected to the housing and a separating arm extending from the straight segment and curves away from the straight segment so that an end of the separating arm is disposed substantially perpendicular to the straight segment and towards an interior of the housing, said separating arm being adapted to separate a top protective layer of the package from each bandage and from a bottom protective layer of the bandage after the roll of packaged bandages has been placed into the housing with the separating arm being inserted between the top protective layer and the roll of packaged bandages, so that the separator is adapted to continually separate the top protective layer from the bandages and from the bottom protective layer as the bandages and the bottom protective layer are pulled through the opening of the housing.

2. The bandage dispenser according to claim 1, further comprising a storage compartment in the housing for receiving the top protective layer that is separated from the roll of bandages by the separator, said compartment keeping the separated top layer from contacting any bandages disposed in the housing.

3. The bandage dispenser according to claim 1, further comprising a support connected to a side wall of the housing, said support adapted to support a roll of bandages placed in the housing.

4. The bandage dispenser according to claim 3, wherein the support comprises a rod.

5. The bandage dispenser according to claim 1, further comprising a cutting device disposed along a top or bottom side of the opening, said cutting device adapted to separate a portion of the bottom protective layer from the roll of bandages when the bottom protective layer is pulled through the opening.

6. The bandage dispenser according to claim 1, wherein the separator further comprises a second separating arm, each separating arm being disposed on an opposite end of the straight segment of the separator, and wherein each separating arm extends in the same direction.

7. A bandage dispenser comprising:
   a housing having an opening in a side wall thereof;
   a plurality of packaged bandages disposed within the housing, the packaged bandages being disposed in a continuous strip, wherein an individually packaged bandage of the plurality of packaged bandages comprises a bandage disposed between a top protective layer and a bottom protective layer, with the top protective layer being removably connected to the bottom protective layer, and wherein said continuous strip of packaged bandages is arranged in a roll; and
   a separator comprising a straight segment connected to the housing near the opening, and a separating arm extending from the straight segment and curving away from the straight segment so that an end of the separating arm is disposed substantially perpendicular to the straight segment and towards an interior of the housing;
   wherein inserting the separating arm between the top protective layer and the bandage causes the separator to separate the top protective layer from the bandages and from the bottom protective layer as the bandages and the bottom protective layer are pulled through the opening of the housing.

8. The bandage dispenser according to claim 7, wherein the top protective layer remains inside the housing after said top protective layer is separated from the bandages and from the bottom protective layer by the separator.

9. The bandage dispenser according to claim 7, further comprising a cutting device disposed along a top or bottom side of the opening, said cutting device adapted to separate a portion of the bottom protective layer from the continuous strip as the bottom protective layer is pulled against the cutting device.

10. The bandage dispenser according to claim 7, wherein the packaged bandages in the continuous strip are separable from one other via perforations in the bottom protective layer that run in a transverse direction to the continuous strip.

11. The bandage dispenser according to claim 7, wherein the separator further comprises a second separating arm, with each separating arm being disposed on an opposite end of the straight segment of the separator, and each separating arm extending in the same direction.

12. The bandage dispenser according to claim 7, further comprising a support for the roll of bandages connected to a side wall of the housing.

13. The bandage dispenser according to claim 12, wherein the support comprises a rod extending through a center of the roll of bandages.

14. The bandage dispenser according to claim 7, wherein the housing further comprises an upper compartment that stores the top protective layer that has been separated from the bandages and lower protective layer to prevent the separated top protective layer from mixing with the roll of bandages in the housing.

* * * * *